(12) United States Patent
Kase et al.

(10) Patent No.: US 9,205,002 B2
(45) Date of Patent: Dec. 8, 2015

(54) THERAPEUTIC TAPE

(71) Applicants: Kenzo Kase, Albuquerque, NM (US); Yukari Takeda, Tokyo (JP)

(72) Inventors: Kenzo Kase, Albuquerque, NM (US); Yukari Takeda, Tokyo (JP)

(73) Assignee: KINESIO IP LLC, Albuquerque, NM (US)

( * ) Notice: Subject to any disclaimer, the term of this patent is extended or adjusted under 35 U.S.C. 154(b) by 182 days.

(21) Appl. No.: 13/755,764

(22) Filed: Jan. 31, 2013

(65) Prior Publication Data

US 2013/0310774 A1    Nov. 21, 2013

Related U.S. Application Data

(60) Provisional application No. 61/648,539, filed on May 17, 2012.

(51) Int. Cl.
*A61F 13/02* (2006.01)
*A61F 13/00* (2006.01)

(52) U.S. Cl.
CPC ........... *A61F 13/0253* (2013.01); *A61F 13/025* (2013.01); *A61F 2013/0028* (2013.01); *A61F 2013/0077* (2013.01)

(58) Field of Classification Search
CPC   A61F 13/0203; A61F 13/0246; A61F 13/025
USPC ............. 602/55, 54, 75, 22; 604/385.03, 290, 604/307; 128/888, 889
See application file for complete search history.

(56) References Cited

U.S. PATENT DOCUMENTS

| 3,457,919 | A | | 7/1969 | Harbard | |
|---|---|---|---|---|---|
| 5,861,348 | A | * | 1/1999 | Kase | 442/184 |
| 6,191,338 | B1 | * | 2/2001 | Haller | 602/55 |
| D621,051 | S | | 8/2010 | Kase et al. | |
| D621,052 | S | | 8/2010 | Kase | |
| D621,053 | S | | 8/2010 | Kase | |
| D621,054 | S | | 8/2010 | Kase | |
| 7,902,420 | B2 | | 3/2011 | Kase | |
| 2010/0210987 | A1 | * | 8/2010 | Lu | 602/54 |
| 2010/0298747 | A1 | | 11/2010 | Quinn | |
| 2011/0056621 | A1 | * | 3/2011 | Quinn | 156/269 |

FOREIGN PATENT DOCUMENTS

| EP | 1 716 829 | 11/2006 |
|---|---|---|
| JP | 2006326327 | 12/2006 |
| JP | D1337219 | 8/2008 |
| JP | D1337220 | 8/2008 |
| JP | D1337287 | 8/2008 |

(Continued)

OTHER PUBLICATIONS

U.S. Appl. No. 29/405,807, filed Nov. 7, 2011, also assigned to Kinesio IP LLC.

International Search Report for International Patent Application No. PCT/US2013/024095, mailed May 3, 2013 (14 pages).

(Continued)

*Primary Examiner* — Victoria J Hicks
*Assistant Examiner* — Tarla Patel
(74) *Attorney, Agent, or Firm* — Finnegan, Henderson, Farabow, Garrett & Dunner, LLP

(57) ABSTRACT

In various embodiments, therapeutic tapes are provided. The therapeutic tapes can include a repeating pattern resembling a human fingerprint. The repeating pattern can provide improved therapeutic benefits when applied to a patient's skin.

10 Claims, 5 Drawing Sheets

(56) References Cited

FOREIGN PATENT DOCUMENTS

| JP | 2010-163592 | 7/2010 |
| JP | D1433989 | 2/2012 |
| WO | WO/97/07759 | 3/1997 |

OTHER PUBLICATIONS

International Preliminary Report on Patentability, with Written Opinion of the International Searching Authority, for International Application No. PCT/US2013/024095, dated Nov. 18, 2014, (9 pages).

* cited by examiner

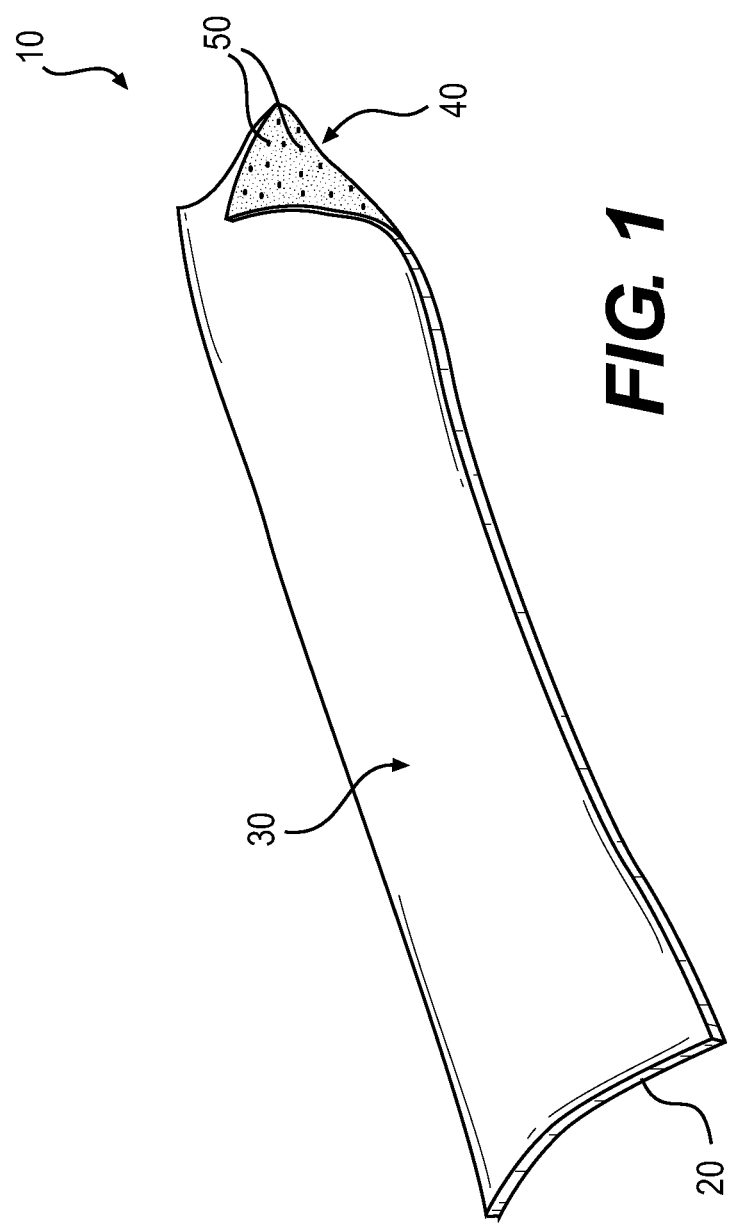

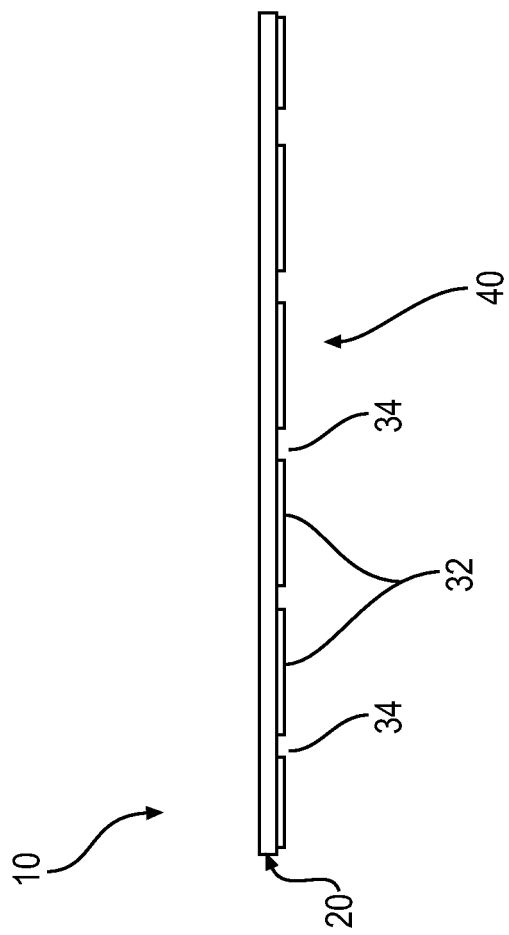

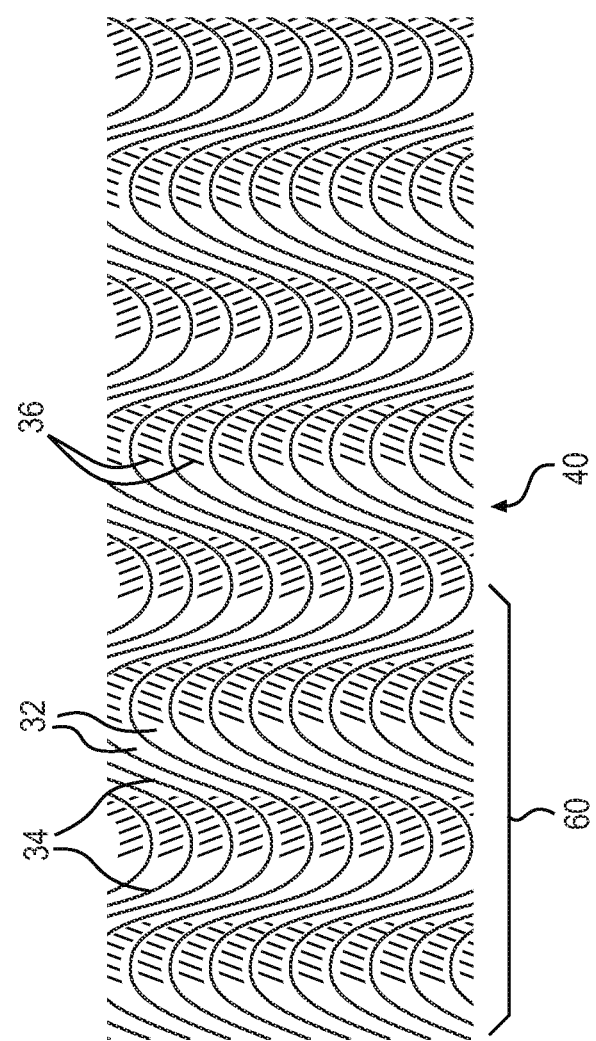

THERAPEUTIC TAPE

CROSS-REFERENCE TO RELATED APPLICATIONS

This application claims priority under 35 U.S.C. §119 to U.S. Provisional Application No. 61/648,539, which was filed on May 17, 2012.

The present disclosure relates generally to systems and methods for treating tissue using flexible materials such as tape.

BACKGROUND INFORMATION

Currently, various types of tapes are used to support tissue and affect muscles, joints, and other tissues. For example, elongated tapes can be placed on a patient's skin to support underlying tissues or provide other therapeutic benefits. In some cases, therapeutic tapes can be flat, elongated materials that simply provide structural support. In other cases, the tapes can include specific surface patterns, which engage a person's skin and can provide therapeutic benefits by stimulating underlying tissues including the epidermis, dermis, and surrounding connective tissue, muscles, and cells. Such surface patterns can include patterns formed by ridges and grooves.

Currently available tapes are effective for certain uses, but may be improved to more specifically target stem cells and provide therapeutic benefits such as immune support, muscle stimulation, tissue regeneration and repair, removal of congestion and toxins, improved blood flow, and/or maintenance of proper fluid balance. Accordingly, the present disclosure provides devices and methods for improved treatment of tissues using flexible materials.

In certain embodiments, the present disclosure provides therapeutic tape. The tape can comprise a layer of flexible material having a first surface and second surface opposite the first surface. The second surface can be configured to be positioned against skin and can comprise an adhesive for securing the second surface to the skin. The second surface can include a repeating pattern mimicking a human fingerprint.

In certain embodiments, a method of providing therapy to a person is provided. The method can include selecting a layer of flexible material having a first surface and a second surface opposite the first surface. The second surface can be configured to be positioned against skin and comprise a repeating pattern mimicking a human fingerprint. The method can further comprise securing the second surface to the skin using an adhesive.

BRIEF DESCRIPTION OF SEVERAL VIEWS OF THE DRAWINGS

FIG. 1 illustrates a therapeutic tape according to certain embodiments of the present disclosure.

FIG. 2 illustrates a cross-sectional view of a therapeutic tape according to certain embodiments of the present disclosure.

FIG. 3A illustrates a surface of a therapeutic tape according to certain embodiments of the present disclosure.

BRIEF SUMMARY OF THE EXEMPLARY EMBODIMENTS

Figure 3B:
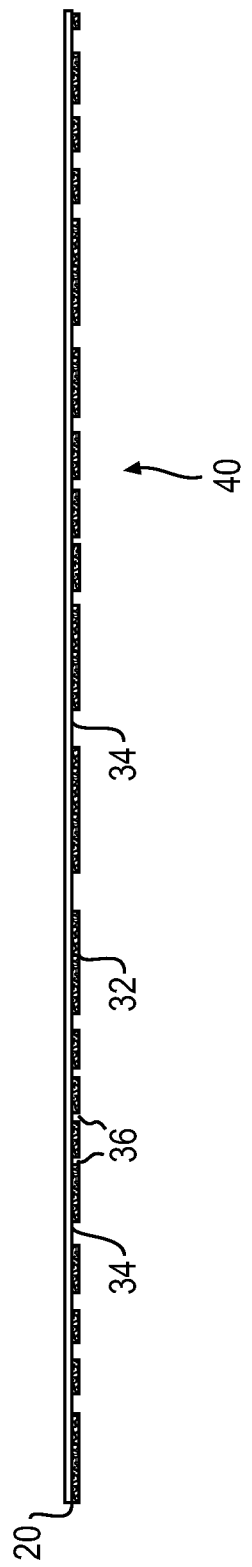
FIG. 3B illustrates a cross-section of FIG. 3A.

The present disclosure provides therapeutic tapes and methods of using therapeutic tapes to treat patients. In various embodiments, as shown in FIG. 1, the therapeutic tape 10 can include a layer of flexible material 20. The flexible material 20 can have a first surface 30 and a second surface 40 opposite the first surface 30. The second surface 40 can be configured to be positioned against skin. In addition, the second surface can comprise an adhesive 50, for securing the second surface 40 to the skin. In certain embodiments, the therapeutic tape 10 can include a repeating pattern on the second surface, as described further below.

Therapeutic tapes, according to the present disclosure, can be used generally for treatment of musculoskeletal disorders and to provide numerous other therapies. The therapeutic tape 10 can be placed on the skin of a person or animal to provide a variety of therapeutic treatments. For example, in some cases the therapeutic tape 10 can be placed around a joint, around a musculoskeletal structure or on certain portions of the skin to provide support, provide a massaging structure to underlying tissues, or assist in other therapeutic measures. In certain embodiments, the therapeutic tape 10 is configured to provide stimulation to underlying structures, including cellular structures (e.g., stem cells), to improve psychological functions, improve immune function, remove toxins, stimulate healthy tissue generation, remove toxins and/or congestion, improve blood flow, and/or improve moisture balance.

The therapeutic tape 10, as shown in FIG. 1, can include a variety of features to provide improved treatments. For example, the therapeutic tape 10 can include surface structures that provide improved stimulation of the underlying tissues. For example, in some embodiments, the second surface 40 of the therapeutic tape 10 can include a repeating pattern that mimics a human fingerprint. The repeating pattern can be selected such that the tape provides precise stimulation and avoids overstimulation of underlying tissues. In some embodiments, the repeating pattern can be selected to stimulate the stem cells between the underlying epidermis and dermis. The stimulation of stem cells and other cells or tissues can provide a variety of therapeutic effects, as listed above. It is believed that patterns resembling human fingerprints provide improved therapeutic benefits compared to simply wave-like designs. For example, fingerprint-like patterns are believed to provide an improved massaging and lifting effect during movement to affect underlying structures without overstimulation.

The therapeutic tape, as shown in FIG. 1, can include a variety of different shapes. For example, the therapeutic tape 10 can include an elongated rectangular structure, as shown in FIG. 1, or can include a variety of different shapes. For example, the therapeutic tape can be square, ovoid, circular, oblong, star, or form a variety of crossing shapes such as a "Y," an "M," an "X," an "H," or a "T." In addition, the tape 10 can have a wide range of sizes depending on the desired use and treatment site. For example, a small portion of tape having a round, ovoid, or irregular structure may be used for discrete stimulation of focused anatomic sites (e.g., the sole of the foot, palm of the hand, or specific area on the torso, arms, head, or other anatomic location). Alternatively, large portions of tape can be used to treat larger areas (e.g., a limb, the back, and/or a musculoskeletal structure of a larger animal such as a horse or cattle).

In addition, the therapeutic tape can be formed of a variety of different structural materials. In certain embodiments, the therapeutic tape 10 is formed of a flexible, polymeric material or fabric that provides sufficient structural support and allows a transfer of mechanical stimulation to underlying tissues. In certain embodiments, the therapeutic tape is selected to provide flexibility while having sufficient strength and rigidity to allow stimulation of underlying tissues.

FIG. 2 illustrates a cross-sectional view of a tape 10 according to various embodiments. As discussed above, the second surface 40 of tape 10 can include a pattern and an adhesive. In various embodiments the pattern can be formed from ridges and grooves on the second surface 40 to produce a textured surface. The ridges 32 and grooves 34 can be selected to have various heights and widths. The height of ridges 32 and depth of grooves 34 can be consistent across the second surface, or can vary across the second surface 40. In various embodiments, the height and depth are selected to provide a desired level of stimulation to underlying tissues without causing overstimulation.

The pattern can be formed in a number of ways. For example, in one embodiment, the pattern is formed in the adhesive. As such, the ridges 32 are formed of an adhesive layer having a desired thickness. Alternatively, the ridges can be formed of a separate structural material forming a textured surface, and the adhesive can be applied onto the separate structural material. In some embodiment, the ridges 32 are formed of an adhesive layer having a desire thickness, and the grooves 34 are formed by regions where the adhesive is absent or has a thickness less than the thickness of the ridges 32.

The pattern can be produced using a number of suitable manufacturing processes. For example, as noted above, the pattern can be formed from an adhesive such that ridges 32 are formed where adhesive is present, and grooves 34 are formed in areas where adhesive is absent, or as stated above, exists to a lesser extent. The ridges 32 and grooves 34 can be produced in several ways. For example, an adhesive may be applied using a focused application processes such to apply adhesive only where ridges 32 are desired. Such application process can include a mold or focused dispersal (e.g., with an automated delivery system). Alternatively, adhesive may be applied evenly across the surface 40, and grooves 34 can be formed by removing some or all of the adhesive by scraping or other means.

Figure 4:
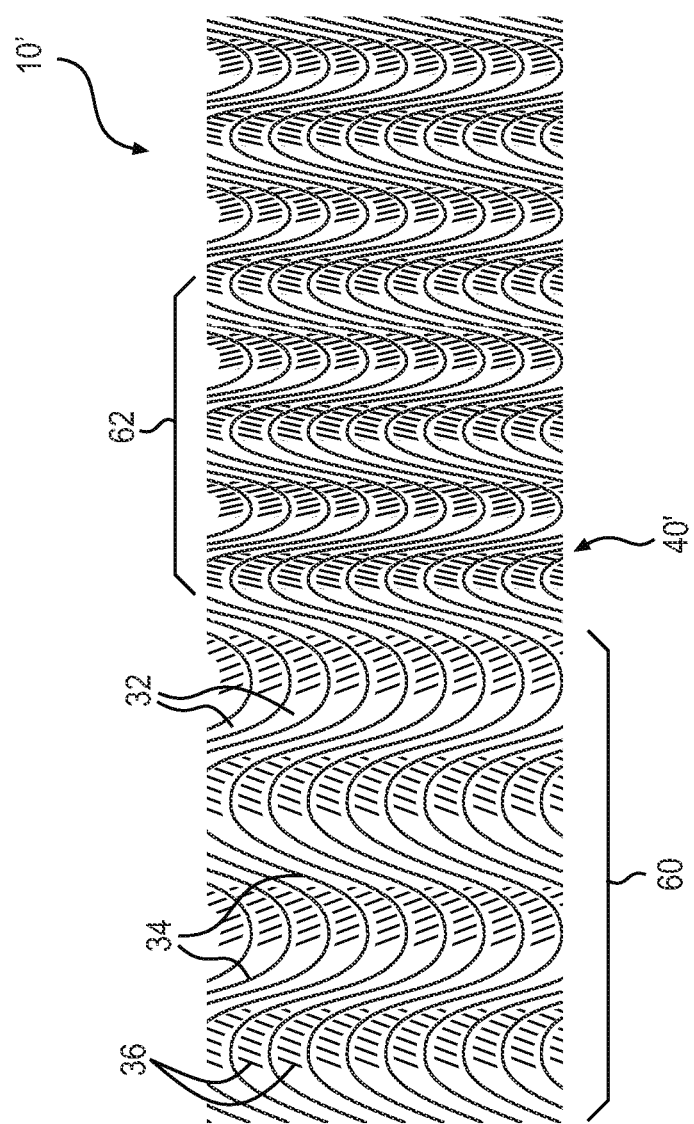
FIG. 4 illustrates a surface of a therapeutic tape according to certain embodiments of the present disclosure.

The specific design of the repeating pattern mimicking a human fingerprint on the second surface 40 can be consistent across the tape length and width or can vary. FIGS. 3A, 3B and 4 illustrate various embodiments of tapes according to the present disclosure. As shown in FIG. 3A, the second surface 40 can include a single pattern design 60 that is repeated across the length of tape 10. Alternatively, the tape 10 can have multiple pattern designs that are repeated at regular or random intervals across the length or width of tape 10. For example, as shown in FIG. 4, the second surface 40' of tape 10' can include two or more pattern designs 60, 62. It will be appreciated that tapes according the present disclosure can include multiple different pattern designs, and the position of specific pattern designs relative to each other may be selected based on the tissue site being treated for the type of therapy to be provided or emphasized. By way of example only, it is also possible that one or the same pattern may be positioned at an angle (e.g., orthogonal) relative to the other, i.e., does not appear to be continuous As noted above, the pattern of tapes 10, 10' can be formed of ridges 32 and groove 34 on the second surface 40, 40'. The ridges can be formed at locations where adhesive is present, while the groove 34 can be formed at locations where adhesive is absent or present to a lesser extent. Further, the width and height of the ridges and grooves may vary. In addition, other grooves 36 may be formed by removing adhesive to produce different patterns. Any pattern mimicking features of human fingerprints and/or combinations of patterns may be used, including those formed on the hand. Such patterns can include circular, ovoid, wave-like or other patterns consistent with a human fingerprint.

The repeating pattern can be selected to provide desired mechanical stimulation to underlying cells, tissue, or other structures. For example, during bending, rotation, compression, or extension, the tape is designed to provide a gentle lifting and massaging effect without causing overstimulation. The gentle lifting and massaging can result in decreased pain, improved blood flow, improved lymphatic drainage, improvement in muscle function and recovery, and/or improvement in joint structure and function.

As noted, the tapes of the present disclosure can be applied to skin to administer therapy. It will be appreciated that the tapes can be applied to human and non-human subjects (e.g., farm animals, horses, domestic pets), to achieve any of the therapeutic benefits discussed above.

What is claimed is:

1. A therapeutic tape comprising:
   a layer of flexible material having a first surface and a second surface opposite the first surface, wherein the second surface is configured to be positioned against skin;
   an adhesive located on the second surface for securing the second surface to the skin; and
   a repeating, fingerprint-shaped pattern formed in the adhesive located on the second surface, wherein the fingerprint-shaped pattern comprises a textured surface that mimics a human fingerprint, wherein the fingerprint-shaped pattern is made up of:
   a plurality of ridges and a plurality of first grooves that extend in a first direction along the adhesive, wherein the ridges are formed where the adhesive is present and the plurality of first grooves are formed where the adhesive is absent or where the adhesive has a first thickness that is less than a second thickness of the ridges; and
   a plurality of second grooves located adjacent to and in between the plurality of first grooves, wherein the plurality of second grooves extend in a second direction.

2. The tape of claim 1, wherein the repeating, fingerprint-shaped pattern includes a wave-like form that is repeated across a length or a width of the second surface.

3. The tape of claim 1, wherein the ridges and the first grooves of the textured surface have a height and a depth selected to allow stimulation of stem cells located between an epidermis and a dermis when the tape is secured to the skin.

4. The tape of claim 1, wherein the repeating pattern comprises a single pattern design.

5. The tape of claim 1, wherein the repeating pattern comprises two or more pattern designs.

6. The tape of claim 5, wherein each pattern design comprises a wave-like pattern.

7. A method of providing therapy to skin, comprising:
   selecting a layer of flexible material having a first surface and a second, textured surface opposite the first surface, wherein the second surface is configured to be positioned against the skin and comprises a repeating, fingerprint-shaped pattern that mimics a human fingerprint, wherein the fingerprint-shaped pattern is made up of a plurality of ridges formed where the adhesive is present, a plurality of first grooves formed where the adhesive is absent or where the adhesive has a first thickness that is less than a second thicknes of the ridges and a plurality of second grooves, located adjacent to and in between the plurality of first grooves wherein the plurality of ridges and the plurality of first grooves extend in a first direction along the second surface, and the plurality of second grooves extends in a second direction; and securing the second surface to the skin using an adhesive.

8. The method of claim 7, wherein the repeating, fingerprint-shaped pattern includes a wave-like form that is repeated across a length or a width of the second surface.

9. The method of claim 7, wherein the ridges and the first grooves of the textured surface have a height and a depth selected to allow stimulation of stem cells bested between an epidermis and a dermis when the tape is secured to the skin.

10. The tape of claim 1, wherein at least one of a height of the plurality of ridges, a width of the plurality of ridges, a depth of the plurality of grooves, or a width of the plurality of grooves varies across the second surface.

* * * * *